US00PP29137P3

(12) United States Plant Patent
Zerr

(10) Patent No.: US PP29,137 P3
(45) Date of Patent: Mar. 20, 2018

(54) **NEW GUINEA *IMPATIENS* PLANT NAMED 'IMGZ0008'**

(50) Latin Name: *Impatiens hawkeri*
Varietal Denomination: IMGZ0008

(71) Applicant: SYNGENTA PARTICIPATIONS AG, Basel (CH)

(72) Inventor: Katharina Zerr, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/330,094

(22) Filed: Aug. 4, 2016

(65) Prior Publication Data

US 2017/0142888 P1 May 18, 2017

Related U.S. Application Data

(60) Provisional application No. 62/254,417, filed on Nov. 12, 2015.

(51) Int. Cl.
*A01H 5/02* (2006.01)

(52) U.S. Cl.
USPC ..... Plt./318.1

(58) Field of Classification Search
USPC ..... Plt./318.1, 318.5, 318.6
CPC ..... A01H 5/0261
See application file for complete search history.

*Primary Examiner* — Kent L Bell
(74) *Attorney, Agent, or Firm* — Dale Skalla

(57) ABSTRACT

A New Guinea *Impatiens* plant named 'IMGZ0008' particularly distinguished by the sharp pattern of the Red Star on the flower on short peduncles on a medium sized well branched plant with deep dark green foliage.

1 Drawing Sheet

Figure 1:
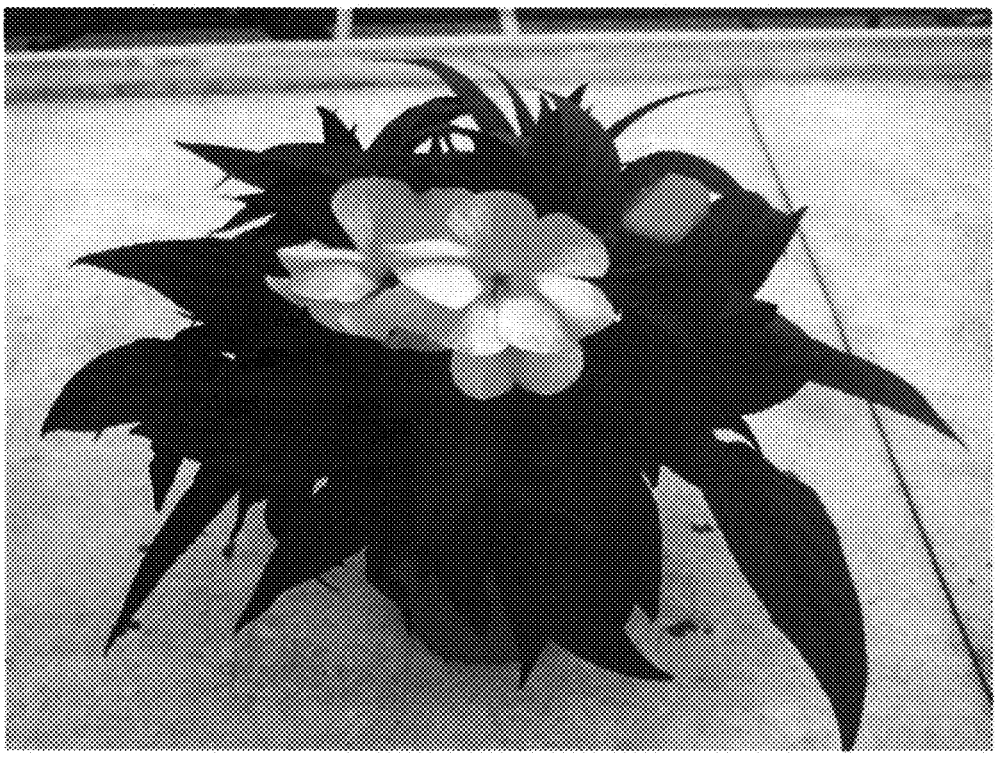
Figure 2:
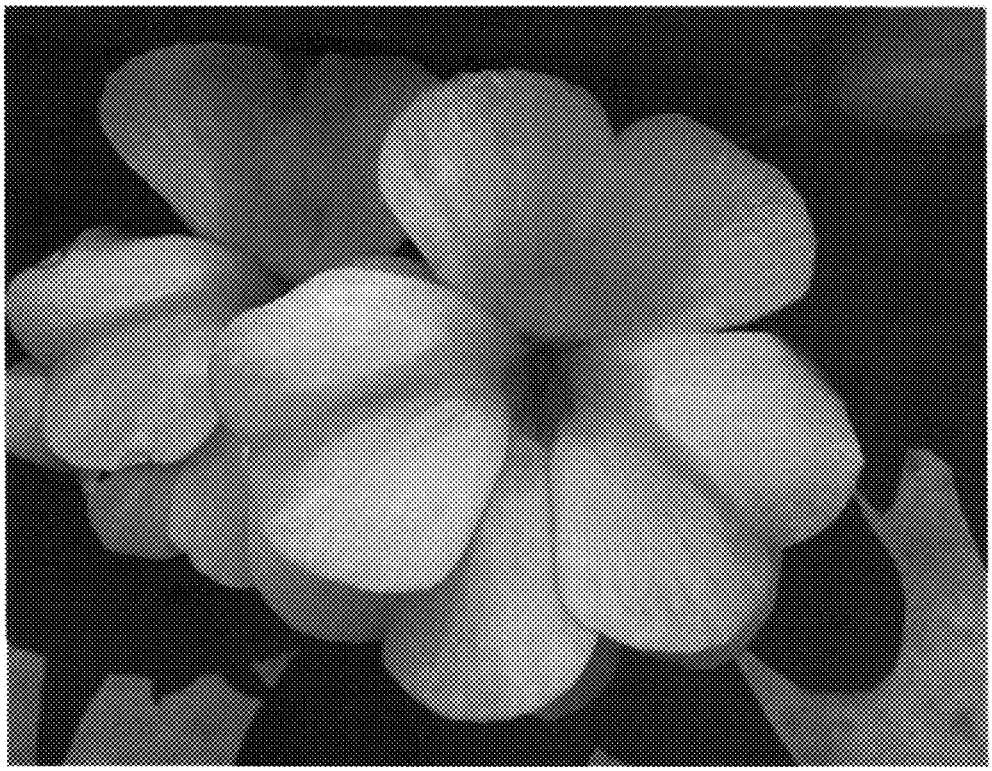

Latin name of the genus and species of the plant claimed: *Impatiens hawkeri.*

Varietal denomination: 'IMGZ0008'.

BACKGROUND OF THE NEW PLANT

The present invention comprises a new New Guinea *Impatiens*, botanically known as *Impatiens hawkeri*, and hereinafter referred to by the variety name 'IMGZ0008'.

'IMGZ0008' is a product of a planned breeding program. The new cultivar has large, flat flowers with a relatively sharp Red Star pattern. Between the Red Star, the spaces are light pink colored. The foliage is very deep dark green with light red veins on the upper and lower side of the leaf. The space between the leaf veins on the upper and lower side is reddish. The plant is medium sized and well branched.

'IMGZ0008' originated from a hybridization made in June 2005 in a controlled breeding environment in Hillscheid, Germany.

The female parent is designated as 'K07-8559-1' and has a red flower color and a compact habit. The male parent is designated as 'K07-8549-1' and is large sized and has a purple star flower pattern.

The resultant seed was sown in November 2005 in a greenhouse in Moncarapacho, Portugal and 'IMGZ0008' was selected there as one flowering plant within the progeny of the stated cross in spring 2006.

The first act of asexual reproduction of 'IMGZ0008' was accomplished when vegetative cuttings were propagated from the initial selection in June 2006 in a controlled environment in Moncarapacho, Portugal.

BRIEF SUMMARY OF INVENTION

Horticultural examination of plants grown from cuttings of the plant initiated in March 2007 in Hillscheid, Germany and continuing thereafter in Enkhuizen The Netherlands, has demonstrated that the combination of characteristics as herein disclosed for 'IMGZ0008' are firmly fixed and are retained through successive generations of asexual reproduction.

'IMGZ0008' has not been observed under all possible environmental conditions. The phenotype may vary significantly with variations in environment such as temperature and light intensity.

A Plant Breeder's Right for this cultivar has not yet been applied for. 'IMGZ0008' has not been made publicly available prior to the effective filing date of this application, notwithstanding any disclosure that may have been made less than one year prior to the effective filing date of this application by the inventor or another who obtained 'IMGZ0008' directly from the inventor.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawing shows typical flower and foliage characteristics of 'IMGZ0008' with colors being as true as possible with an illustration of this type. The photographic drawings show a close-up of the flowers and a flowering plant of the new variety growing in 12 cm pot.

DETAILED BOTANICAL DESCRIPTION

The aforementioned photographs were taken in October 2015 from plants grown in a greenhouse trial in Enkhuizen, The Netherlands. These plants were growing in 12 cm pots and were approximately 15 weeks of age.

The plant descriptions and measurements were taken in October 2015 on 17 week old plants growing in a greenhouse in Enkhuizen, The Netherlands. Cuttings were stuck in week 25 for rooting, planted into 12 cm pots in week 29, and were grown, without pinching, on benches in a greenhouse, initially at a day temperature of 18° C. and night temperature of 16° C. However, day temperatures often raised above 18° C.

Color references are made to The Royal Horticultural Society Colour Chart (R.H.S.) 2001.

TABLE 1

DIFFERENCES BETWEEN THE NEW VARIETY 'IMGZ0008' AND SIMILAR PATENTED VARIETIES

| | 'IMGZ0008' | JP497 ('Sonic Sweet Orange') | JN777 ('Sonic Sweet Cherry') |
|---|---|---|---|
| Flower color: | Red Star | Orange Star | Red/White, no star |
| Flower pattern: | Sharp | Very sharp | Not sharp |
| Habit/vigor: | Medium | Small | Small |
| Branching: | More | Less | Less |

Plant:

*Form, growth and habit.*—Medium sized, mounded, well branched.

*Plant height.*—21.0 cm (without pot), 30 cm (with pot).

*Plant height (inflorescence included).*—20.0-22.0 cm (without pot).

*Plant width.*—35.0 cm.

Roots:

*Number of days to initiate roots.*—7 days at about 22 degrees C.

*Number of days to produce a rooted cutting.*—15-18 days at 22 degrees C.

*Type.*—Fibrous, free branching.

*Color.*—RHS 159A.

Foliage:

*Arrangement.*—Simple leaves, mainly in whorls.

*Young leaf, color upper surface.*—RHS 135A.

*Young leaf, color lower surface.*—Closest RHS 187A.

*Mature leaf, color upper surface.*—RHS 136A.

*Mature leaf, color lower surface.*—Closest to RHS 187A.

*Length.*—Up to 15.0 cm.

*Width.*—Up to 4.0 cm.

*Shape.*—Lanceolate.

*Base shape.*—Lanceolate.

*Apex shape.*—Acuminate.

*Margin.*—Serrulate, with short bristles.

*Texture.*—Slightly waxy and glossy on the upper surface, glabrous on both surfaces.

*Color of veins, upper surface.*—RHS 45C.

*Color of veins, lower surface.*—RHS 187A.

*Petiole color, upper side.*—RHS 45C.

*Petiole color, lower side.*—RHS 187A.

*Length.*—Up to 2.5 cm.

*Diameter.*—0.3 cm.

*Texture.*—Glabrous.

Stem:

*Color of stem.*—RHS 61B.

*Length of stem.*—About 10-16 cm.

*Diameter.*—0.5-1.0 cm.

*Length of internodes.*—Approximately 2 to 6 cm.

*Texture.*—Smooth, glabrous.

*Number of branches.*—6 main branches plus 6-8 side branches per main branch.

*Color of peduncle.*—RHS 134B.

*Length of peduncle.*—1.5-4.0 cm.

*Peduncle diameter.*—0.3-0.5 cm.

*Texture.*—Glabrous.

Inflorescence:

*Blooming habit.*—Continuous flowering from late spring through fall.

*Type of inflorescence.*—Solitary flowers emerge from the upper leaf nodes of the stem.

*Number of flowers per node.*—1-3 open flowers and additional buds in various stages of development.

*Quantity of flowers per plant.*—6 open flowers plus 25-30 (big and small) buds (12 cm pot plant in October).

*Lastingness of individual blooms on the plant.*—About 6-9 days.

*Fragrance.*—None.

Bud (just before opening):

*Color.*—RHS 39A.

*Length.*—Up to 2 cm.

*Width.*—Up to 1.5 cm.

*Shape.*—Ovate.

Immature flowers:

*Color of petals, upper surface.*—RHS N30A +RHS 75B.

*Color of petals, lower surface.*—RHS 39B.

Mature flowers:

*Flower, vertical length.*—7 cm.

*Flower, horizontal width.*—7 cm.

*Flower depth.*—1.5-2.0 cm.

*Color of petals, upper surface.*—RHS 34A (Star color) and RHS 75B (space color between Star).

*Color of petals, lower surface.*—RHS 39A.

*Petal shape.*—Heart shaped.

*Petal apex shape.*—Broadly obcordate.

*Petal margin.*—Entire.

*Petal texture, upper surface.*—Papillose.

*Petal texture, lower surface.*—Papillose.

Calyx:

*Arrangement.*—One large sepal bearing the spur, 2 small, lateral sepals, and 1 fused keel.

*Large sepal(s).*—Color, visible surface: RHS 50C on both sides.

*Length.*—1.9 cm.

*Width.*—1.4 cm.

*Shape.*—Ovate.

*Apex shape.*—Aristate.

*Base.*—Fused with the spur.

*Margins.*—Entire.

*Texture, upper surface.*—Papillose.

*Texture, lower surface.*—Papillose.

*Lateral sepals.*—Color of surface: RHS 41B on both sides.

*Length.*—1.3 cm.

*Width.*—0.6-0.7 cm.

*Shape.*—Ovate.

*Apex shape.*—Acuminate.

*Base.*—Fused.

*Margins.*—Entire.

*Texture, upper surface.*—Glabrous.

*Texture, lower surface.*—Glabrous.

*Keel color.*—From RHS 46A to more brownish tones, closest to RHS 185A.

Spur:

*Color*.—RHS 144C.

*Length*.—4.5-4.8 cm.

*Diameter*.—0.3 cm at the base, 0.1 cm at tip.

Reproductive organs:

*Androecium*.—5 stamen, fused with the anthers hooded.

*Diameter of androeceum*.—0.7 cm.

*Surface color*.—RHS N57B, fading towards margin.

*Pollen amount*.—Plenty.

*Color of pollen*.—RHS 8D.

Gynoecium:

*Pistil*.—One, elongate.

*Pistil length*.—0.6 cm.

*Stigma color*.—RHS N57B.

*Ovary color*.—Dark brown, RHS 183A to RHS 144B (green).

*Fertility/seed set*.—Has not been observed on this hybrid.

*Disease/pest resistance*.—Has not been observed on this hybrid. However, it is known for *Impatiens* New Guinea that it is downy mildew resistant.

What is claimed is:

1. A new and distinct variety of New Guinea *Impatiens* plant named 'IMGZ0008' substantially as illustrated and described herein.

* * * * *